(12) United States Patent
Ruskin

(10) Patent No.: US 8,286,667 B2
(45) Date of Patent: Oct. 16, 2012

(54) PREVENTION OF BACTERIAL ADHESION IRRIGATION CONDUITS

(75) Inventor: Rodney Ruskin, San Rafael, CA (US)

(73) Assignee: A.I. Innovations, N.V., San Rafael, CA (US)

( * ) Notice: Subject to any disclaimer, the term of this patent is extended or adjusted under 35 U.S.C. 154(b) by 551 days.

(21) Appl. No.: 12/383,733

(22) Filed: Mar. 27, 2009

(65) Prior Publication Data

US 2009/0250137 A1 Oct. 8, 2009

Related U.S. Application Data

(60) Provisional application No. 61/123,119, filed on Apr. 3, 2008.

(51) Int. Cl.
*F16L 9/14* (2006.01)

(52) U.S. Cl. ..... 138/141; 138/137; 138/146; 428/36.91; 428/36.92

(58) Field of Classification Search ............... 138/146, 138/137, 141; 428/36.91, 36.92
See application file for complete search history.

(56) References Cited

U.S. PATENT DOCUMENTS

| | | | | |
|---|---|---|---|---|
| 3,426,473 A * | 2/1969 | Cardarelli et al. | ............... | 43/131 |
| 4,526,932 A * | 7/1985 | Imazaki et al. | ............... | 525/326.7 |
| 5,084,315 A * | 1/1992 | Karimi et al. | ................. | 428/36.6 |
| 5,332,160 A * | 7/1994 | Ruskin | ........................... | 239/542 |
| 5,375,626 A * | 12/1994 | Fears | ............................ | 138/103 |
| 5,576,106 A | 11/1996 | Kerbow et al. | | |
| 5,631,042 A | 5/1997 | Becker et al. | | |
| 6,305,428 B1 * | 10/2001 | Nakamura et al. | ............ | 138/126 |
| 6,511,724 B1 * | 1/2003 | Siour et al. | ................. | 428/36.91 |
| 6,558,798 B2 * | 5/2003 | Zhong et al. | .................. | 428/420 |
| 6,686,012 B1 * | 2/2004 | Molnar et al. | ............. | 428/36.91 |
| 6,776,195 B2 | 8/2004 | Blasko et al. | | |
| 6,821,928 B2 | 11/2004 | Ruskin | | |
| 6,830,794 B2 * | 12/2004 | Cartledge et al. | .......... | 428/36.91 |
| 7,862,873 B2 * | 1/2011 | Yankovitz et al. | ......... | 428/36.91 |

(Continued)

FOREIGN PATENT DOCUMENTS

WO  WO 2007/021782 A1  2/2007

OTHER PUBLICATIONS

Partial International Search Report mailed on Jul. 23, 2009, for International Application No. PCT/US2009/038587 filed on Mar. 27, 2009.

(Continued)

*Primary Examiner* — James Hook
(74) *Attorney, Agent, or Firm* — Christie, Parker & Hale, LLP

(57) ABSTRACT

A water transmission tubing for controlling the flow of water under pressure comprises a tubular inner liner of generally uniform cross-sectional configuration continuous with the length of the tubing and having an anti-bacterial agent for preventing the growth of bacteria on the inside wall of the tube. The inner liner contains a dispersed slip additive that forms a low friction surface inside the tubing for preventing adherence of slime to the inside of the tubing. The slip additive can comprise a fluoroelastomer, a fluoropolymer, a silicone resinous material, or mixtures thereof. The liner can be a separate inner layer of a multi-layer dripline, a monolayer form of the dripline or the inside of a drip irrigation emitter. The invention is particularly useful in subsurface treatment of wastewater.

10 Claims, 3 Drawing Sheets

U.S. PATENT DOCUMENTS

2006/0275572 A1* 12/2006 Bonnet et al. .............. 428/36.91

OTHER PUBLICATIONS

3M; Dyneon; "Fluoroelastomers Copolymers;" (Website); <http://solutions.3m.com/wps/portal/3M/en_US/dyneon_fluoropolymers/Home/Products_and_Solutions/Fluoroelastomers-FKMs/Fluoroelastomers/>; 2009; Minnesota, USA.

DuPont Performance Elastomers; "Viton fluoroelastomer;" (Website) <http://www.dupontelastomers.com/Products/Viton/viton.asp>; 1998-2009; USA.

PSP Inc.; (Website); <http://www.pspglobal.com/viton-apa-article-17.html>; 1997-2009, Problem Solving Products, Inc.; Colorado, USA.

Viton FreeFlow; "For unbeatable performance the easy choice is Viton FreeFlow," (Journal); 2006; USA.

Wikipedia, a Free Encyclopedia (Website); "FKM;" <http://en.wikipedia.org/wiki/FKM>; Dec. 27, 2008; GNU Free Documentation License, USA.

Wikipedia, a Free Encyclopedia (Website); "VITON;" <http://en.wikipedia.org/wiki/Viton>; Dec. 29, 2008; GNU Free Documentation License, U.S.A.

* cited by examiner

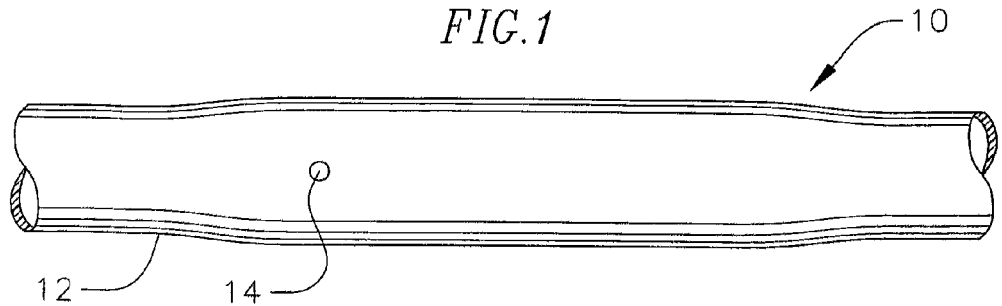
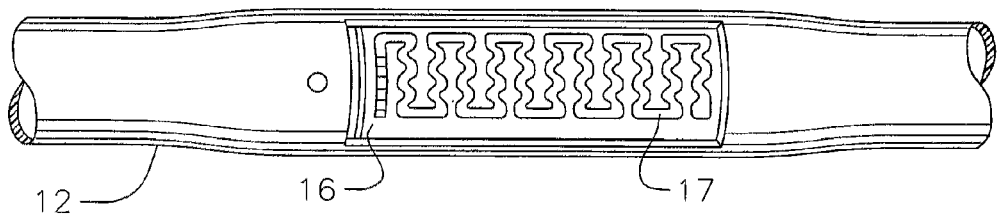
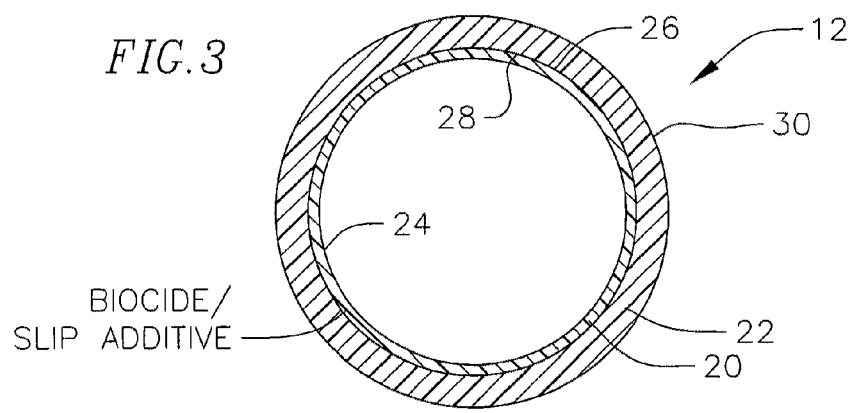
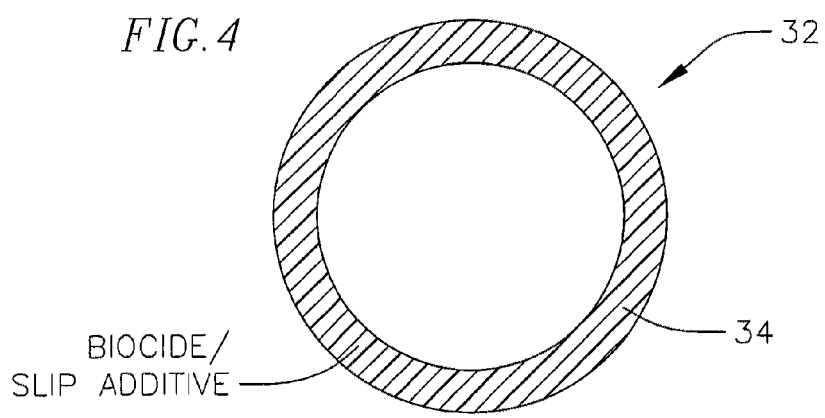

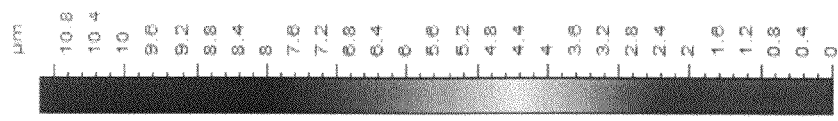
Fig. 6
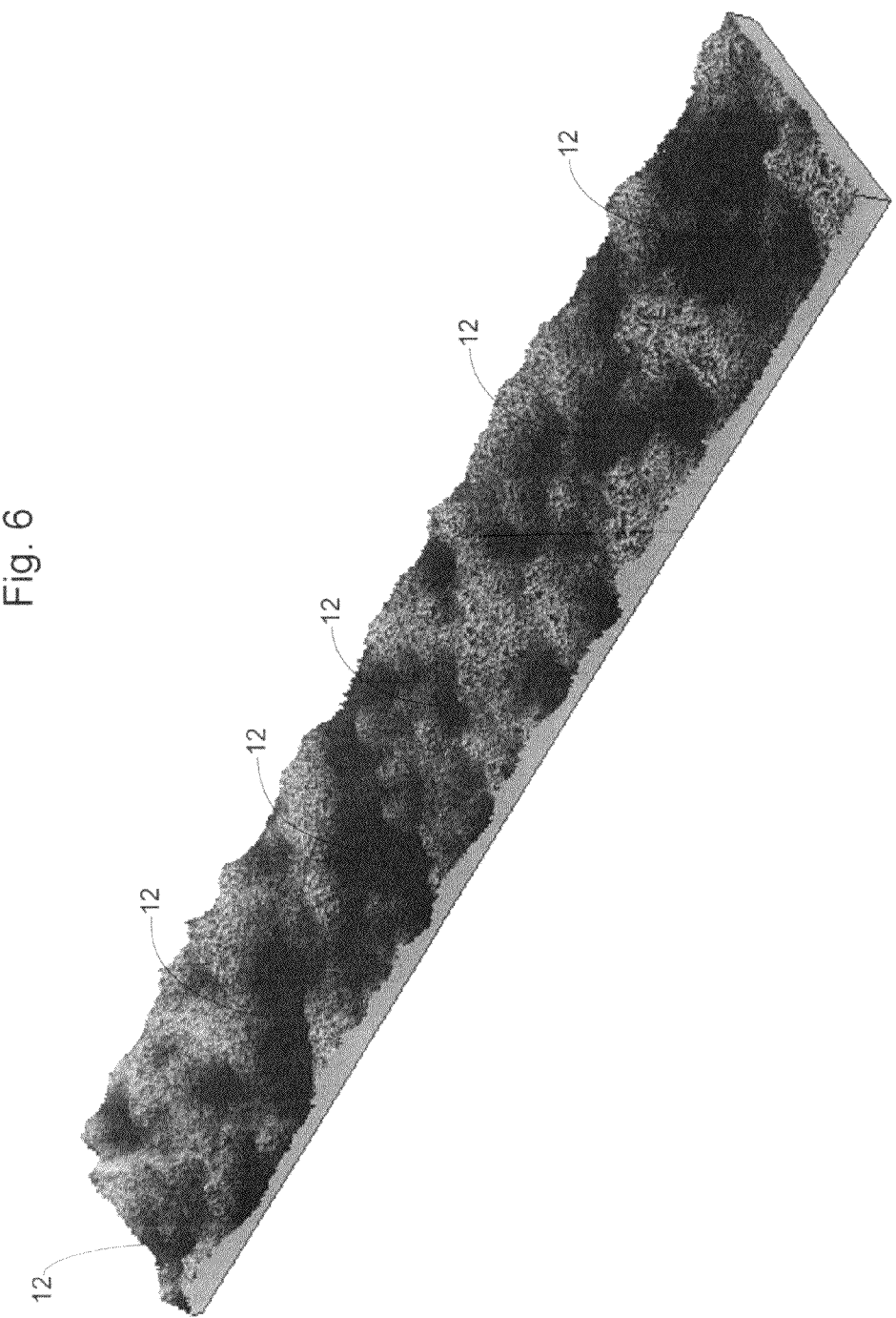

PREVENTION OF BACTERIAL ADHESION IRRIGATION CONDUITS

CROSS REFERENCE

This application claims priority to U.S. Provisional Application No. 61/123,119, filed Apr. 3, 2008, incorporated herein in its entirety by this reference.

FIELD OF INVENTION

This invention relates to drip irrigation, and more particularly, to a drip irrigation conduit having a low friction interior surface or lining that resists adherence and growth of slime during use, especially in subsurface wastewater disposal systems.

BACKGROUND OF INVENTION

Drip irrigation systems usually include a continuous irrigation water supply line with separate emitter units installed on the line or in the line, usually at regular intervals. Irrigation water flows through the supply line under pressure, and a small amount of water drips out at the intervals where the drip emitters are installed.

A common approach for controlling drip flow involves use of separate emitter units installed in or on the supply line. The emitter unit receives water flowing in the supply line and passes it through a labyrinth or other passageway that produces a large pressure drop and discharges the water at a uniform drip rate.

Because of life forms in the water flowing through the supply line, especially in waste water systems, slime forms along the inside walls of the tube. As the slime grows, the inner wall loses its smooth surface. Laminar flow within the tube is obstructed by the irregular surface, thereby causing an undesired pressure drop within the tube.

In drip irrigation systems, the growth of the slime also can occur within the emitter unit. Slime grows along the path of the labyrinth and across the outlet hole. As the slime grows within the emitter, the flow of water can be reduced or shut off.

To solve the slime problem, drip irrigation supply lines have been developed containing an anti-bacterial agent for killing the slime-forming bacteria. One example is the subsurface wastewater disposal system from Geoflow, Inc., Corte Madera, Calif. Geoflow's dripline tubing, sold under the mark WASTEFLOW, contains an anti-bacterial interior lining for preventing growth of bacteria on the wall of the tube and preventing undesired buildup of slime on the insides of the tubing and the emitters. This anti-bacterial dripline is described in U.S. Pat. No. 5,332,160 to Ruskin, incorporated herein by reference.

Although the anti-bacterial dripline provides an improvement in reducing the growth of slime on the inside walls of the tubing and the emitters, the present invention provides a further improvement in preventing slime and other bacterial or organic growth from adhering to the inside walls of the tubing and the emitters, especially in wastewater disposal systems where bacterial growth is more of a problem.

SUMMARY OF THE INVENTION

Briefly, one embodiment of the invention comprises a composition for use in forming a drip irrigation tubing or an inner liner for the tubing. The composition comprises an extrudable thermoplastic polymeric resinous material and a slip agent, preferably a fluoropolymer, a fluoroelastomer, or silicone resinous material, dispersed in the polymeric material. The slip agent is contained in the thermoplastic polymeric material at an effective level that produces a sufficiently low friction surface that essentially prevents adhesion of slime or other bacterial or organic growth on the surface of the irrigation tubing or the inner liner made from the composition.

Another embodiment of the invention comprises a water transmission conduit or tubing having an inner wall surface for contact with water traveling in the conduit. The material which forms the inner wall comprises a thermoplastic polymeric material containing an anti-bacterial agent which kills slime-forming bacteria and inhibits the growth of slime on the inner wall of the tubing. The inner wall also contains a dispersed slip additive. The slip additive migrates to the surface of the inner wall to reduce its coefficient of friction sufficiently to form a smooth, low friction surface that prevents slime or other bacterial or organic growth from attaching to the surface during use.

Another form of the invention comprises a composition for use in forming a drip irrigation tubing or an inner liner for the tubing, comprising an extrudable thermoplastic polymeric resinous material, an anti-bacterial agent dispersed in the polymeric material, and a slip additive dispersed in the polymeric material. The anti-bacterial agent is contained at an effective level to prevent the growth of bacteria on the wall of the tube. The slip additive comprises a fluorinated polymer, a fluoroelastomer, or silicone resin contained at an effective level sufficient to produce a low friction surface that prevents adhesion of slime-forming growth without retarding the effectiveness of the anti-bacterial agent.

The invention provides an improvement in preventing adhesion of bacterial growth or slime on the inside surface of drip irrigation tubes, and drip irrigation emitters, and is especially useful in wastewater disposal systems.

These and other aspects of the invention will be more fully understood by referring to the following detailed description and the accompanying drawings.

BRIEF DESCRIPTION OF THE DRAWINGS

FIG. 1 is a schematic perspective view illustrating an irrigation supply line according to the principles of this invention.

FIG. 2 is a fragmentary view illustrating an emitter in the supply line shown in FIG. 1.

FIG. 3 is a cross-sectional view illustrating one embodiment of the invention which includes a low friction anti-bacterial inner lining inside a drip irrigation supply line.

FIG. 4 is a cross-sectional view illustrating an alternative embodiment comprising a monolayer form of the invention.

FIG. 6 is a gray-tone surface roughness profile of the inside surface of a drip irrigation tubing according to this invention.

DETAILED DESCRIPTION

Figure 5:
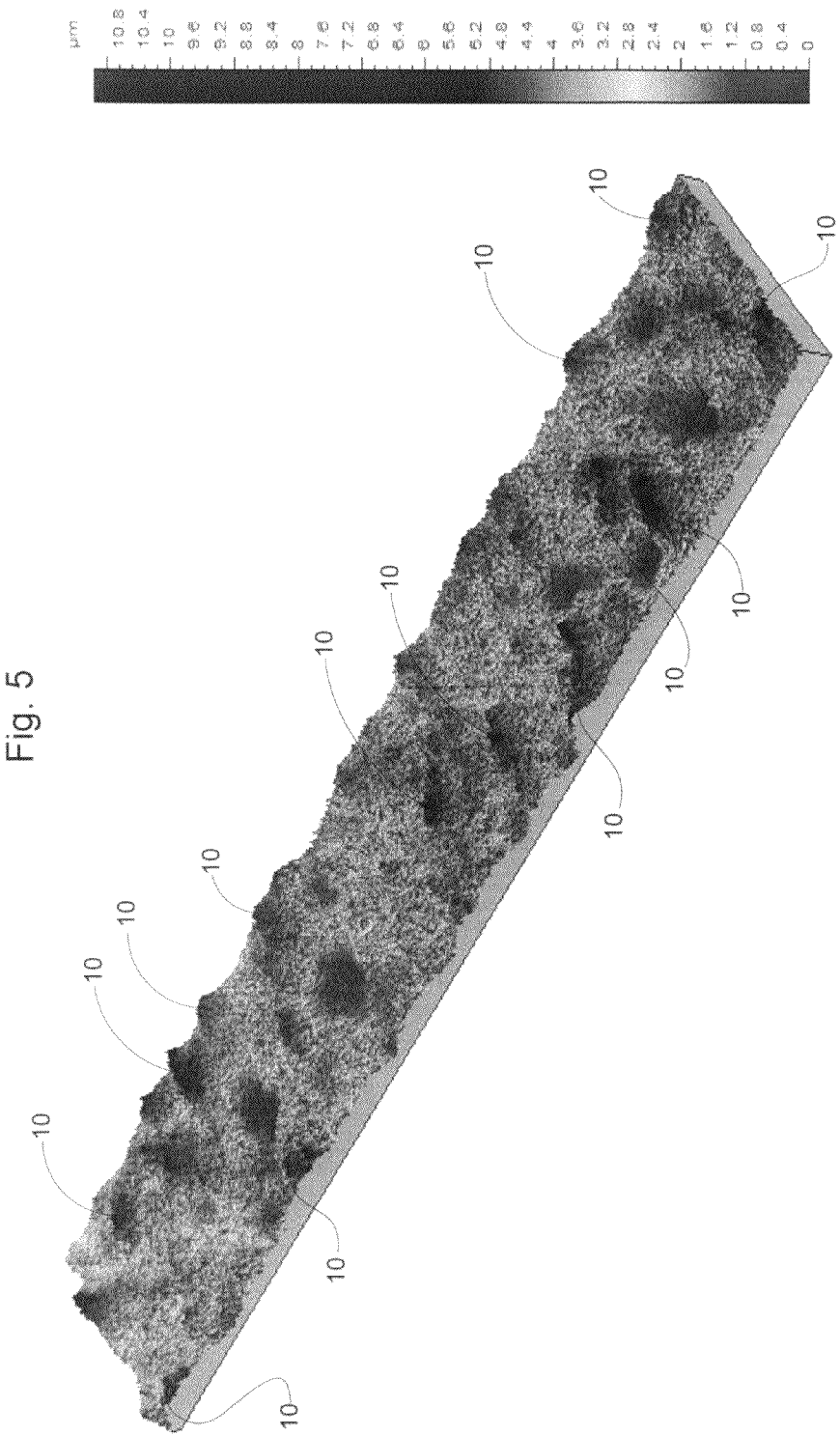
FIG. 5 is a gray-tone surface roughness profile of the inside surface of a conventional drip irrigation tubing.

FIG. 1 is a schematic view illustrating an irrigation supply line 10 according to principles of this invention. A supply line comprises a conduit 12 having a plurality of fluid discharge ports 14 spaced apart longitudinally along the length of the supply line.

FIG. 2 is a fragmentary elevational view illustrating an emitter 16 disposed within the conduit 12. The preferred embodiment uses an emitter inside the conduit. In an alternate embodiment, the emitter can be attached outside the conduit.

Although the invention is shown in a drip irrigation system, the invention may also be used in other water or fluid transmission systems in which slime-forming or other harmful bacteria inhabit the water or the fluid transmitted therein. These systems include subsurface wastewater disposal systems, such as those available from Geoflow, Inc. under the designation WASTEFLOW.

The emitter 16 has a water-entry port (not shown) for allowing water to flow from the inside of the conduit 12 into a labyrinth 17 disposed on the outer surface of the emitter. The labyrinth 17 is a narrow passage that circuitously channels the water to generate a turbulent flow. The turbulent flow keeps fine particles in suspension. The water flows through the labyrinth 17 and out of the fluid discharge port 14 and into the soil (not shown).

FIG. 3 is a cross-sectional view of the conduit 12. The conduit preferably has a circular cross section. However, the principles of this invention apply to any cross sectional shape. The conduit 12 comprises an inner liner 20 and an outer layer 22. The inner liner 20 and the outer layer 22 each have a circular cross section and a uniform wall thickness. The inner liner 20 has an inside surface 24 facing toward the center of the conduit to form a tubular enclosed region for containing water or other fluids within the conduit. The inner liner 20 also has an outside surface 26. The outer layer 22 has an inside surface 28 in contact with the outside surface 26 of the inner liner 20. The conduit is made from an extrudable thermoplastic polymeric material, and the layers 20 and 22 are bonded together by coextrusion techniques. The outer layer 22 has an outside surface 30 exposed to the soil, the sunlight and air.

In one embodiment of the invention, the inner liner 20 contains an anti-bacterial agent for preventing the growth of bacteria on the inside surface 24 of the irrigation lines. A preferred anti-bacterial agent is tributyltin maleate (TBTM), although other anti-bacterial agents can be used effectively with the present invention. The preferred anti-bacterial agent such as TBTN does not dissolve in water and does not migrate through the plastic that forms the conduit. It protects the wall of the tube without dosing chemicals to the water and killing bacteria in the water. The inner liner also contains a dispersed slip additive described below.

The outer layer 22 is made of a material and has a thickness to inhibit the migration or movement of the anti-bacterial agent from the inner layer 20, through the outer layer 22, and to the exterior of the conduit. The outer layer 22 is preferably made of a linear low-density polyethylene (LLDPE) and has a broad range of molecular weights.

In the two-layer drip irrigation tube, the inner liner contains the anti-bacterial agent and the dispersed slip additive, also referred to as an anti-stick agent. The inner liner is preferably made from the same polymeric resinous material normally used in drip irrigation tubing or dripline, i.e., an extrudable thermoplastic polymeric material which can include polyolefins such as low density polyethylene, although other similar polyethylene materials, such as LLDPE or HDPE, or polypropylene also can be used. The slip additive is dispersed in the resinous material used in forming the inner liner. The slip additive material comprises a polymeric material that can migrate to the surface during use and form a surface of micro-thin surface roughness, characterized by a reduced coefficient of friction when compared with the surface of a conduit made from the same resinous material in the absence of the slip additive. Suitable materials used for the slip additive include fluoropolymers, fluoroelastomers, and silicone resins. In one embodiment, the fluoroelastomers can be those generally known as FKM polymers, defined in ASTM D1418. These materials may contain hexafluoropropylene (HFP) and vinylidene fluoride ($VF_2$), and in some instances are further polymerized with tetrafluoroethylene (TFE). They are characterized by a high fluorine content, usually greater than 50% and more commonly greater than about 65%. The fluoroelastomers also may comprise perfluoroelastomers (FFKM).

More specifically, the slip additive material can comprise:
(a) a fluoroelastomer, a fluoropolymer, a silicone resin, or mixtures thereof, or
(b) a fluoroelastomer comprising vinylidene fluoride and hexafluoropropylene, or
(c) vinylidene fluoride, hexafluoropropylene, fluoroethylene, or mixtures thereof.

A presently preferred material is the fluoroelastomer available under the designation VITON from DuPont, characterized as a copolymer containing hexafluoropropylene and vinylidene fluoride, or a terpolymer containing hexafluoropropylene, vinylidene fluoride, and tetrafluoroethylene. In one embodiment, the fluoroelastomer comprises VITON FreeFlow blended as an additive with the extruded polymeric material. Another preferred fluoropolymer is polytetrafluoroethylene (PTFE) and/or vinylidene fluoride.

Use of the slip additive in the inner liner produces a smooth, shiny, non-stick surface. The slippery, low friction surface is believed to reduce adhesion of bacteria and slime to the inside surface of the tube or its liner. The inner surface of the liner or tubing of this invention is characterized by a reduction in coefficient of friction measured by a surface roughness having average height differences of 10 microns or less, more preferably 8 microns or less. In one embodiment, the surface roughness of the present invention is characterized by surface height differences not greater than about 6.5 microns. The low friction surface of this invention was tested by applying markings from an ink pen which were easily rubbed off by finger pressure. The same markings are not easily removed when applied to a conventional drip irrigation tubing surface made from the same polymeric material in the absence of the slip additive.

The slip additive, in one embodiment, is present in an amount greater than 2:1,000 parts by weight additive to total resin contained in the liner or tubing material. The slip additive is used in the resinous liner material in an amount in excess of the amount a similar extrusion processing aid would be used for extruding the resinous liner material or other inner layer or tubing. In one embodiment, at least twice the usual quantity (in wt %) of non-stick material is used (when compared with use as an extrusion processing aid) so that the low friction additive material will migrate or bloom to the surface over time after extrusion, even at room temperature.

FIG. 4 shows an alternative single layer conduit 32. The single layer conduit can have a wall structure 34 with the anti-bacterial agent concentration uniformly distributed in the wall. The slip additive also is dispersed generally uniformly in the single layer tubular wall material. The two-layer conduit of FIG. 3 is less expensive to manufacture using coextrusion than extruding a single layer with a concentration gradient.

In an alternative form the invention, a mono-layer drip irrigation tubing can be used in the absence of the anti-bacterial agent, or with reduced concentration of the anti-bacterial agent, and with the same level of slip additive to inhibit adhesion of bacterial growth or slime.

EXAMPLE

A drip irrigation conduit 10,000 feet in length was coextruded. The inside liner contained 0.08% by weight VITON FreeFlow dispersed in LLDPE. The extruded material contained 4% by weight of the extrusion polymer component known as INGENIA IP1121, a blend of LLDPE and 2% VITON FreeFlow extrusion additive, dispersed in the LLDPE extrusion material, yielding a VITON content of 0.08% by weight. The outer wall of the coextrusion was LLDPE. The inner wall of the tubing was very smooth and shiny, much more so than a standard extruded LLDPE irrigation conduit. The inner wall of the liner containing the non-stick agent was resistant to adhesion of bacterial slime.

To test the low friction, non-stick characteristics of the inner liner, a black ink permanent marking pen and a blue ink ball point pen were used to mark the inside wall of the VITON-treated tube. Both easily rubbed off, using only a dry cloth, demonstrating that the non-stick additive is being bloomed to the surface.

The same inks applied to a conventional LLDPE tube, in the absence of the non-stick additive, marked the tube permanently.

Comparative tests were conducted between a drip irrigation tubing containing VITON in an inner lining of LDPE (Test Sample (a)) and a conventional LDPE drip irrigation tubing from Netafim USA (Test Sample (b)) in the absence of a non-stick additive. The tests were conducted in the absence of an anti-bacterial agent. Surface roughness tests were conducted on both test items by an independent test laboratory using profilometry measurements based on axial chromatism techniques. Surface measurements (referred to as profilometry measurements) were conducted by Micro Phonetics, using a Nanovea 3D Profilometer. The surface measurements involved axial chromatism techniques using a white light source, where light passes through an objective lens with a high degree of chromatic aberration.

The objective lens's refractive index varies in relation to the wavelength of the light. In effect, each separate wavelength of the incident white light will refocus at a different distance from the lens (different height). When the measured sample is within the range of possible heights, a single monochromatic point is focalized and forms an image. Due to the confocal configuration of the system, only the wavelength in focus will pass through the spatial filter with high efficiency, thereby causing all other wavelengths to be out of focus.

If the sample is composed of several transparent or semi-transparent thin layers, each interface between adjacent layers will reflect the light of a different wavelength, and the spectrum of detected lights will be composed of a series of spectral peaks. The chromatic aberration technique allows all interfaces to be detected and their positions to be measured simultaneously.

The spectral analysis is done using a diffraction grating. This deviates each wavelength at a different position intercepting a line of CCD, which in turn indicates the position of the maximum intensity and allows direct correspondence to the Z-axis irrigation height position.

The tests conducted on the two test samples of drip tubing are summarized as follows:

Probe Specifications

| Measurements Range | 400 μm |
|---|---|
| Z Resolution (nm) | 12 |
| Z Accuracy (nm) | 60 |
| Lateral Resolution (μm) | 1.3 |

Parameters

| Probe | 400 μm |
|---|---|
| Acquisition rate | 30 and 100 Hz |
| Averaging | 1 |
| Measured surface | 3 mm × 0.5 mm |
| Step size | 4 μm × 4 μm |
| Scanning Mode | Constant speed |

Procedures

Surface thresholded
Filled in non-measured points
Surface form removed
Profile extracted
Surface roughness calculated from measurement area
3D surface generated Differences in surface roughness were measured by five different test procedures. The following roughness values were measured:

Sq—root-mean-square height
Sp—maximum peak height
Sv—maximum pit height
Sz—maximum height
Sa—arithmetical mean height The test results showed greater height differences in each test parameter for the conventional product when compared with the smaller height differences for the present invention. As shown in the following test data summary, the surface roughness of the conventional product showed an average of 80% or greater height differences compared with the present invention, for each of the test procedures.

Height Parameters

|  | Test Sample (a) | Test Sample (b) | % Increase |
|---|---|---|---|
| Sq | 0.883 | 1.640 | 86 |
| Sp | 3.230 | 2.780 | 110 |
| Sv | 3.130 | 7.310 | 130 |
| Sz | 6.350 | 14.100 | 122 |
| Sa | 0.708 | 1.280 | 81 |

Surface roughness profiles are shown in gray-scale in FIGS. 5 and 6. The surface roughness profiles are shown in color in the attached Appendix. The profile of FIG. 5 illustrates surface roughness on the inside surface of the conventional material (Test Sample (b)). FIG. 6 illustrates surface roughness on the inside surface of the drip irrigation tubing of this invention (Test Sample (a)). The test points shown at 10 in FIG. 5 were the highest in elevation in that sample. The darkened areas shown at 12 in FIG. 6 were generally lower in elevation and more spread out, revealing a generally smoother surface. The highest test point in Sample (b) (FIG. 5) was 10.8 μm, whereas no test points in Sample (a) (FIG. 6) were higher than 6.4 μm.

Thus, the non-stick additive is blended into the extruded material at an excess level sufficient to cause the non-stick material to bloom to the surface to produce a smoother, lower friction surface, resulting in reduced adhesion of impurities such as bacteria.

The use of the non-stick additive, in producing a lower friction surface, also is useful in systems subject to long intervals of down time, where the system can be flushed during start-up to effectively remove the growth from inside the tube.

The present invention has been described with respect to its use in forming drip irrigation tubing or an inner lining for irrigation conduits. The invention also applies to use of the compositions described herein in forming various types of drip irrigation emitters and the water flow contacting surfaces thereof.

What is claimed is:

1. A water transmission tubing for controlling the flow of water under pressure, comprising:
    an irrigation conduit having a tubular inner wall having an inner surface for contact with water traveling in the conduit,
    the structural component of the tubular inner wall consisting of an extrudable thermoplastic polyolefin material, in which the polyolefin material forming said inner wall is selected from the group consisting of LDPE, LLDPE, HDPE, and polypropylene,
    an anti-bacterial agent dispersed throughout the polyolefin material so as to prevent the growth of slime on the inner surface of the tubular inner wall caused by contact between the flow of water and the inner surface, and
    a slip additive blended with and dispersed in the polyolefin material in a sufficient amount such that the inner wall, in an extruded form thereof, provides a smooth inner surface that inhibits adhesion of slime and other bacterial or organic growth to the inner surface,
    in which the slip additive comprises one of (a)-(c):
    (a) a fluoroelastomer, a fluoropolymer, or mixtures thereof, or
    (b) a fluoroelastomer comprising vinylidene fluoride and hexafluoropropylene, or
    (c) vinylidene fluoride, hexafluoropropylene, fluoroethylene, or mixtures thereof.

2. Apparatus according to claim 1 in which the irrigation conduit comprises a drip irrigation emitter, a drip irrigation supply tubing, or a drip irrigation supply tubing adapted for wastewater disposal.

3. Apparatus according to claim 1 in which the anti-bacterial agent comprises tributyltin maleate.

4. Apparatus according to claim 1 in which the tubing comprises a multi-layer irrigation conduit having a tubular outer wall surrounding and bonded to the tubular inner wall which comprises an inner layer of the conduit, and in which the tubular outer wall contains an absence of the anti-bacterial agent and/or the slip additive.

5. Apparatus according to claim 1 in which the conduit comprises a mono-layer tubing with the anti-bacterial agent and slip additive dispersed in the wall of the tubing.

6. Apparatus according to claim 1 in which the slip additive comprises a fluoroelastomer containing at least 50% fluorine content by weight.

7. Apparatus according to claim 1 in which the inner surface of the tubing comprises a smooth, non-stick surface characterized by a surface variation of not greater than about 10 microns via profilometry measurement, or at least 25% reduction in height compared with a conventional extruded thermoplastic polyolefin tubing of the same material not containing the slip additive.

8. Apparatus according to claim 1 in which the slip additive produces a smooth inner surface with decreased surface roughness compared with the same tubing not containing the slip additive.

9. Apparatus according to claim 1 in which the inner surface is characterized by a surface roughness having average height differences of 10 microns or less.

10. Apparatus according to claim 1 in which the slip additive is present in an amount greater than 2:1,000 parts by weight additive to total resin contained in the inner wall of the conduit.

* * * * *

UNITED STATES PATENT AND TRADEMARK OFFICE
CERTIFICATE OF CORRECTION

| | | |
|---|---|---|
| PATENT NO. | : 8,286,667 B2 | Page 1 of 1 |
| APPLICATION NO. | : 12/383733 | |
| DATED | : October 16, 2012 | |
| INVENTOR(S) | : Rodney Ruskin | |

It is certified that error appears in the above-identified patent and that said Letters Patent is hereby corrected as shown below:

On the Title Page, Item (54) and in the Specification, Column 1, line 1

Title     After "ADHESION"

Insert -- IN --

Signed and Sealed this
Twenty-ninth Day of September, 2015

Michelle K. Lee
*Director of the United States Patent and Trademark Office*